(12) United States Patent
Kim et al.

(10) Patent No.: US 9,149,241 B2
(45) Date of Patent: Oct. 6, 2015

(54) METHOD OF GENERATING IMAGE BY USING MULTI-ENERGY RADIATION DATA AND APPARATUS THEREFOR

(75) Inventors: Sung-su Kim, Yongin-si (KR); Hyun-hwa Oh, Hwaseong-si (KR); Young-hun Sung, Hwaseong-si (KR); Jae-hyun Kwon, Hwaseong-si (KR); Seok-min Han, Seongnam-si (KR); Dong-goo Kang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 422 days.

(21) Appl. No.: 13/591,963

(22) Filed: Aug. 22, 2012

(65) Prior Publication Data
US 2013/0051648 A1   Feb. 28, 2013

(30) Foreign Application Priority Data

Aug. 31, 2011   (KR) .................. 10-2011-0087534

(51) Int. Cl.
| | |
|---|---|
| G06K 9/00 | (2006.01) |
| A61B 6/00 | (2006.01) |
| G01N 23/06 | (2006.01) |
| A61B 8/08 | (2006.01) |

(52) U.S. Cl.
CPC .............. *A61B 6/482* (2013.01); *A61B 6/5205* (2013.01); *G01N 23/06* (2013.01); *A61B 6/4035* (2013.01); *A61B 6/4241* (2013.01); *A61B 6/467* (2013.01); *A61B 6/502* (2013.01); *A61B 6/5235* (2013.01); *A61B 6/56* (2013.01); *A61B 8/5207* (2013.01); *G01N 2223/423* (2013.01)

(58) Field of Classification Search
None
See application file for complete search history.

(56) References Cited

U.S. PATENT DOCUMENTS

| | | | |
|---|---|---|---|
| 7,580,505 B2* | 8/2009 | Kang et al. ............... | 378/57 |
| 8,761,485 B2* | 6/2014 | Jang et al. ............... | 382/132 |
| 2005/0084073 A1 | 4/2005 | Seppi et al. | |
| 2007/0140419 A1 | 6/2007 | Souchay | |
| 2007/0183568 A1* | 8/2007 | Kang et al. ............... | 378/57 |
| 2008/0187095 A1 | 8/2008 | Boone et al. | |
| 2009/0052612 A1 | 2/2009 | Wu et al. | |
| 2009/0135994 A1 | 5/2009 | Yu et al. | |
| 2009/0147919 A1 | 6/2009 | Goto et al. | |

(Continued)

FOREIGN PATENT DOCUMENTS

| | | |
|---|---|---|
| JP | 2009-247521 A | 10/2009 |
| KR | 10-0719350 B1 | 5/2007 |

(Continued)

OTHER PUBLICATIONS

European Office Action issued Dec. 6, 2012 in counterpart European Patent Application No. 12182627.5-1265 (9 pages, in English).

(Continued)

*Primary Examiner* — Tahmina Ansari
(74) *Attorney, Agent, or Firm* — NSIP Law

(57) ABSTRACT

A method of generating an image by using multi-energy radiation data and an apparatus therefor is provided. The method includes receiving multi-energy radiation data including a plurality of pieces of radiation data indicating an inner portion of a subject with respect to a plurality of radioactive rays in different energy bands, respectively, generating, based on the received multi-energy radiation data, radiation data of a radioactive ray in an energy band that is different from the different energy bands, and generating a radiation image of the subject based on the generated radiation data.

17 Claims, 9 Drawing Sheets

(56) References Cited

U.S. PATENT DOCUMENTS

| | | |
|---|---|---|
| 2010/0014737 A1 | 1/2010 | Rührnschopf et al. |
| 2011/0164797 A1* | 7/2011 | Jang et al. ............... 382/130 |
| 2012/0101733 A1* | 4/2012 | Han et al. ............... 702/19 |
| 2013/0051648 A1* | 2/2013 | Kim et al. ............... 382/132 |

FOREIGN PATENT DOCUMENTS

| | | |
|---|---|---|
| KR | 10-2010-0059496 A | 6/2010 |
| KR | 10-2011-0016527 A | 2/2011 |
| WO | WO 2011/037344 A2 * | 3/2011 |

OTHER PUBLICATIONS

Williamson, Jeffrey F. et al. "On two-parameter models of photon cross sections: Application to dual-energy CT imaging," Medical Physics, vol. 33, No. 11, Nov. 2006. XP12091921 (16 pages, in English).

Rehfeld, Niklas S. et al. "Single and dual energy attenuation correction in PET/CT in the presence of iodine based contrast agents," Medical Physics, vol. 35, No. 5, May 2008. XP12116058 (11 pages, in English).

* cited by examiner

METHOD OF GENERATING IMAGE BY USING MULTI-ENERGY RADIATION DATA AND APPARATUS THEREFOR

CROSS-REFERENCE TO RELATED APPLICATIONS

This application claims the benefit of Korean Patent Application No. 10-2011-0087534, filed on Aug. 31, 2011, in the Korean Intellectual Property Office, the entire disclosure of which is incorporated herein by reference for all purposes.

BACKGROUND

1. Field

The following description relates to methods and apparatuses to generate a radiation image, such as, for example, methods and apparatuses to generate a radiation image representing the inside of a subject by using multi-energy radiation data.

2. Description of Related Art

Medical image systems that utilize radiation in order to create images radiate X-rays to a subject, such as, for example, the human body, and acquire a radiation image from X-rays transmitting through the subject. A degree at which X-rays are absorbed into a material of the subject that is radiated depends on a kind or a density of the material or an energy band of the X-rays. For example, an absorption coefficient of bone is high in relation to an absorption coefficient of soft tissue. Thus, contrast between soft tissue and bone is high, thereby clearly distinguishing soft tissue from bone in a radiation image. However, since different tissues of soft tissue have similar absorption coefficients with respect to X-rays in a single energy band, the tissues have similar intensity even in a radiation image, thereby making it difficult to distinguish one type of tissue from another in a radiation image.

SUMMARY

In one general aspect, there is provided a method of generating a radiation image, the method including receiving multi-energy radiation data including a plurality of pieces of radiation data indicating an inner portion of a subject with respect to a plurality of radioactive rays in different energy bands, respectively, generating, based on the received multi-energy radiation data, radiation data of a radioactive ray in an energy band that is different from the different energy bands, and generating a radiation image of the subject based on the generated radiation data.

The general aspect of the method may further provide that the energy band that is different from the different energy bands is determined based on an entire energy band, the entire energy band being determined by combining the different energy bands of the plurality of radioactive rays.

The general aspect of the method may further provide that the energy band that is different from the different energy bands exists outside of the entire energy band.

The general aspect of the method may further provide that an upper limit of the energy band that is different from the different energy bands is less than a lower limit of the entire energy band.

The general aspect of the method may further provide that the energy band that is different from the different energy bands is determined by any one of the different energy bands.

The general aspect of the method may further provide that the generating of the radiation data includes determining an attenuation characteristic and generating the radiation data of the radioactive ray in the energy band that is different from the different energy bands based on the determined attenuation characteristic, the determining of the attenuation characteristic being based on one or more selected from the group consisting of the plurality of pieces of radiation data.

The general aspect of the method may further provide that the generated radiation data of the radioactive ray in the energy band that is different from the different energy bands is based on linearity of the determined attenuation characteristic.

The general aspect of the method may further provide that the determined attenuation characteristic includes one or more selected from the group consisting of an attenuation characteristic by a photoelectric effect and an attenuation characteristic by Compton scattering.

The general aspect of the method may further provide that the generating of the radiation data includes determining intensity of a pixel of each of the plurality of pieces of radiation data, determining intensity of the radiation data of the radioactive ray in the energy band that is different from the different energy bands, and generating the radiation data of the radioactive ray in the energy band that is different from the different energy bands based on the determined intensity of the radiation data, the determining of the intensity of the pixel being based on each of the plurality of pieces of radiation data, the determining of the intensity of the radiation data being based on intensity of each of the plurality of pieces of radiation data.

The general aspect of the method may further provide that the determining of the intensity of the pixel includes determining first intensity of first radiation data of the plurality of pieces of radiation data and determining second intensity of second radiation data of the plurality of pieces of radiation data, and the determining of the intensity of the radiation data includes determining intensity of the radioactive ray in the energy band that is different from the different energy bands based on linearity between the determined first intensity and the determined second intensity.

The general aspect of the method may further provide that the intensity includes one or more selected from the group consisting of intensity by a photoelectric effect and intensity by Compton scattering.

The general aspect of the method may further provide that the plurality of radioactive rays in the different energy bands is detected on an energy band basis from a radioactive ray that has passed through the subject.

The general aspect of the method may further provide that the plurality of radioactive rays in the different energy bands have different peak energy values.

The general aspect of the method may further provide that the generating of the radiation image includes generating a radiation image of the subject based on one or more selected from the group consisting of the plurality of pieces of radiation data and the generated radiation data.

The general aspect of the method may further provide that the generating of the radiation image further includes generating a first radiation image of the subject, generating a second radiation image of the subject, and generating the radiation image of the subject based on the first radiation image and the second radiation image, the generating of the first radiation image being by using one or more selected from the group consisting of the plurality of pieces of radiation data, the generating of the second radiation image being by using the generated radiation data.

In another general aspect, there is provided a computer-readable recording medium storing a computer-readable program for executing a method of generating a radiation image.

In yet another general aspect, there is provided an apparatus to generate a radiation image, the apparatus including an input unit configured to receive multi-energy radiation data including a plurality of pieces of radiation data indicating an inner portion of a subject with respect to a plurality of radioactive rays in different energy bands, respectively, an image processor configured to generate radiation data of a radioactive ray in an energy band that is different from the different energy bands and a radiation image of the subject based on the generated radiation data, the generated radiation data being based on the received multi-energy radiation data, and an output unit configured to output the generated radiation image.

The general aspect of the apparatus may further provide that the image processor includes a radiation data generator and a radiation image generator, the radiation data generator being configured to generate, based on the received multi-energy radiation data, the radiation data of the radioactive ray in the energy band that is different from the different energy bands, the radiation image generator being configured to generate the radiation image of the subject based on the generated radiation data.

The general aspect of the apparatus may further provide that the radiation data generator includes a separator, a characteristic determiner, and a generator, the separator being configured to extract each of the plurality of pieces of radiation data from the received multi-energy radiation data, the characteristic determiner being configured to determine an attenuation characteristic based on one or more selected from the group consisting of each of the plurality of pieces of extracted radiation data, the generator being configured to generate radiation data of the plurality of radioactive rays in the different energy bands based on the determined attenuation characteristic.

The general aspect of the apparatus may further provide that the radiation image of the subject is generated based on one or more selected from the group consisting of the plurality of pieces of radiation data and the generated radiation data.

Other features and aspects may be apparent from the following detailed description, the drawings, and the claims.

Figure 1:
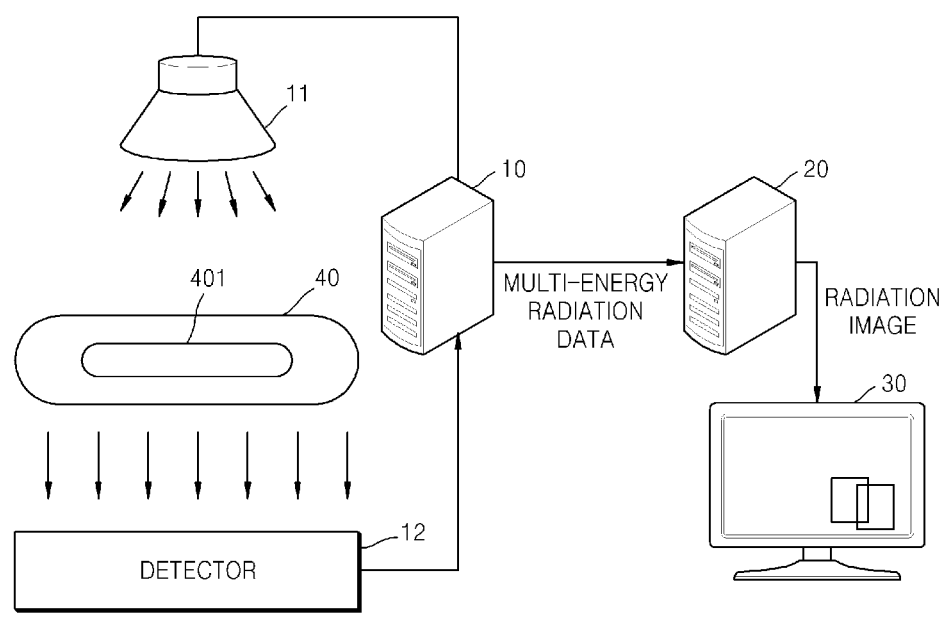
FIG. 1 is a configuration diagram illustrating a medical image system according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 is a configuration diagram illustrating a medical image system according to an example embodiment. Referring to FIG. 1, the medical image system of the example embodiment includes a multi-energy radiation data generating apparatus 10, a radiation image generating apparatus 20, and an image display device 30. The multi-energy radiation data generating apparatus 10 generates a plurality of pieces of radiation data corresponding to radioactive rays in different energy bands that have passed through an inner portion of a subject 40. Here, each of the pieces of radiation data indicates fundamental data of a radiation image representing the inner portion of the subject 40. In this example, the subject 40 includes a human body, but is not limited thereto. The subject 40 may be one of various objects, such as, for example, creatures, materials, and the like, that can be represented by a radiation image.

In general, a radioactive ray indicates an aggregate of energy having a form of a particle or an electric wave emitted when an unstable radionuclide is converted to a more stable radionuclide. Representative examples of a radioactive ray include an ultrasonic wave, an alpha ray, a beta ray, a gamma ray, a X-ray, a neutron ray, an electronic wave used for broadcasting and communication, an infrared ray, and a visible ray. An X-ray, which may harm the human body by causing an ionizing phenomenon, generally represents a radioactive ray in the example embodiment. However, the radioactive ray of the example embodiment is not limited thereto. Although an X-ray is assumed as the radioactive ray in the example embodiment for convenience of description, any type of radioactive ray may be implemented in place of the X-ray. In addition, a radioactive ray is generated in a form of a radiant ray having a transmitting power, which is generated when electrons collide with a subject at a high speed. For example, a radioactive ray is generated from the surface of an anode immediately when electrons generated from a filament of a cathode heated by a high voltage collide with the surface of the anode.

Referring to FIG. 1, the multi-energy radiation data generating apparatus 10 is connected to a radiation generator 11 and a detector 12. The radiation generator 11, the detector 12, or a combination thereof may be included as a unit in the multi-energy radiation data generating apparatus 10 or may operate separately from the multi-energy radiation data generating apparatus 10. The radiation generator 11 generates a radioactive ray in response to a control signal input from the multi-energy radiation data generating apparatus 10. According to an example embodiment, the radioactive ray generated by the radiation generator 11 has a wide energy band, such as, for example, an energy band from about 10 keV to about 60 keV, that corresponds to an energy band of tungsten.

The detector 12 detects a radioactive ray that was generated by the radiation generator 11 and transmitted through the subject 40. In general, the detector 12 generates an electric signal corresponding to an intensity of the detected radioactive ray and provides the generated electric signal to the multi-energy radiation data generating apparatus 10. The multi-energy radiation data generating apparatus 10 generates radiation data corresponding to the radioactive ray based on the received electric signal from the detector 12. In general, the detector 12 includes a plurality of devices to convert a radioactive ray to an electric signal. A representative example of the devices is a photodiode to convert light, such as, for example, a radioactive ray, to an electric signal, but is not limited thereto. Each of the devices of the detector 12 converts the radioactive ray to an electric signal. The multi-energy radiation data generating apparatus 10 generates radiation data by using the electric signal from the detector 12.

The multi-energy radiation data generating apparatus 10 generates multi-energy radiation data including a plurality of pieces of radiation data respectively corresponding to a plurality of radioactive rays in different energy bands that have passed through the subject 40. For example, the plurality of pieces of radiation data respectively correspond to a radioactive ray in an energy band from about 10 keV to about 20 keV and a radioactive ray in an energy band from about 20 keV to about 30 keV from among the radioactive rays that have passed through the subject 40. The multi-energy radiation data generating apparatus 10 transmits the generated multi-energy radiation data to the radiation image generating apparatus 20. In this example, the multi-energy radiation data includes fundamental data of a single radiation image as a single piece of radiation data or fundamental data of a plurality of radiation images as a set of a plurality of pieces of radiation data.

Based on the multi-energy radiation data received from the multi-energy radiation data generating apparatus 10, the radiation image generating apparatus 20 generates radiation data of a radioactive ray having an energy band that is different from the different energy bands of the radioactive rays that have passed through the subject 40, and generates a radiation image using the generated radiation data.

Figure 2:
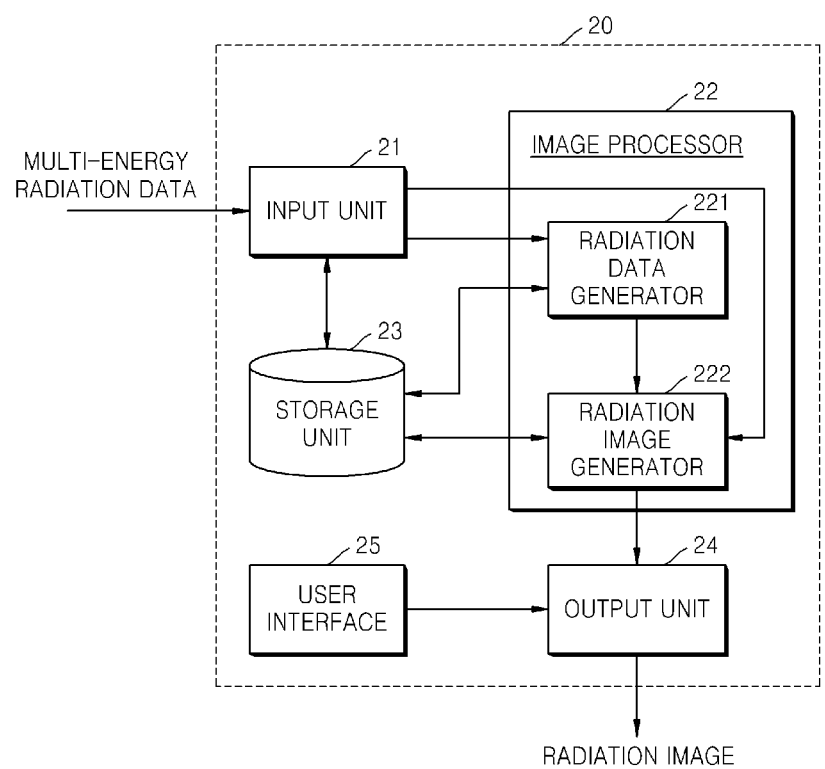
FIG. 2 is a block diagram illustrating a radiation image generating apparatus of FIG. 1, according to an example embodiment.

FIG. 2 is a block diagram illustrating a radiation image generating apparatus 20 of FIG. 1, according to an example embodiment. Referring to FIG. 2, the radiation image generating apparatus 20 includes an input unit 21, an image processor 22, a storage unit 23, an output unit 24, and a user interface 25. However, the radiation image generating apparatus 20 is not limited to the above-referenced configuration.

For example, the radiation image generating apparatus 20 may further include a communication device (not shown) to transmit radiation images generated by the radiation image generating apparatus 20 to an external device, and receive data from the external device. The external device may include another medical image system located at a remote location, a general-use computer system, a facsimile machine, and the like. In addition, the communication device may transmit and receive data to and from the external device via a wired/wireless network. The wired/wireless network includes, but is not limited to, the Internet, a Local Area Network (LAN), a Wireless LAN (WLAN), a Wide Area Network (WAN), a Personal Area Network (PAN), and the like.

The input unit 21 receives multi-energy radiation data. The multi-energy radiation data includes a plurality of pieces of radiation data respectively corresponding to a plurality of radioactive rays. The plurality of radioactive rays is in different energy bands.

Figure 3:
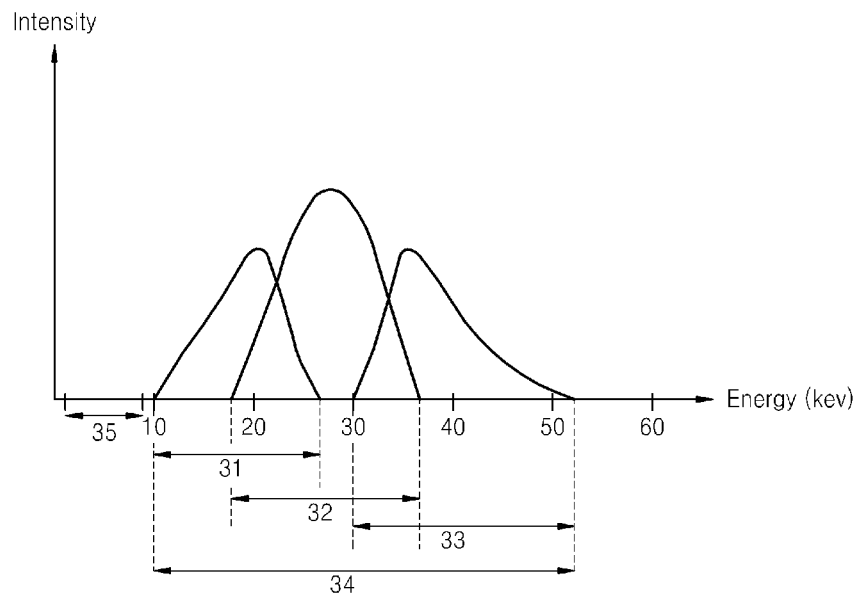
FIG. 3 is a graph illustrating an example of energy spectra of radioactive rays in different energy bands.

FIG. 3 is a graph illustrating an example of energy spectra of radioactive rays in different energy bands. Referring to FIG. 3, the plurality of radioactive rays include a radioactive ray having an energy band 31, a radioactive ray having an energy band 32, and a radioactive ray having an energy band 33. In general, an energy band indicates a range of energy determined by an upper limit and a lower limit of energy of a radioactive ray. An energy spectrum, represented in the form of a graph, indicates that a relationship between a variation of energy and the intensity of a radioactive ray. While not being limited thereto, a basic unit of intensity is the number of photons of a radioactive ray, and a basic unit of energy is keV.

As described above, multi-energy radiation data is generally generated by the multi-energy radiation data generating apparatus 10. However, according to another example embodiment, multi-energy radiation data is generated by the radiation image generating apparatus 20. In this case, the radiation generator 11 and the detector 12 are controlled by the radiation image generating apparatus 20. However, for convenience of description, only an example embodiment in which multi-energy radiation data is generated by the multi-energy radiation data generating apparatus 10 is described herein.

Figure 4:
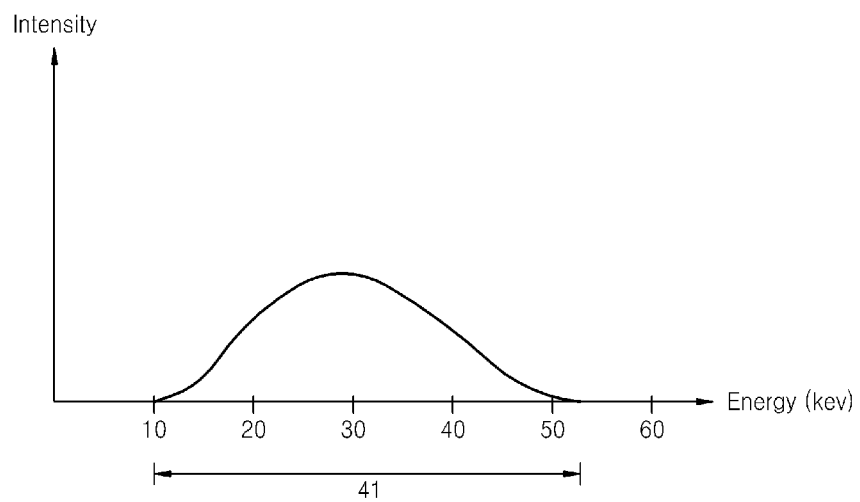
FIG. 4 is a graph illustrating an energy spectrum of a radioactive ray generated by a radiation generator of FIG. 1, according to an example embodiment.

FIG. 4 is a graph illustrating an energy spectrum of a radioactive ray generated by the radiation generator 11 of FIG. 1, according to an example embodiment. Referring to FIG. 4, the multi-energy radiation data generating apparatus 10 uses the radiation generator 11 to generate a source radioactive ray having a single energy band 41. In this example, the single energy band 41 indicates a wide energy band defined by about 10 keV to about 53 keV. In addition, as described above, a basic unit of intensity is the number of photons of a radioactive ray, and a basic unit of energy is keV.

Therefore, according to an example embodiment, the multi-energy radiation data generating apparatus 10 uses the radiation generator 11 to generate a radioactive ray in a single energy band. In this case, the radioactive ray generated by the multi-energy radiation data generating apparatus 10 is distinguished as a source radioactive ray from the radioactive rays in different energy bands described above.

Figure 5:
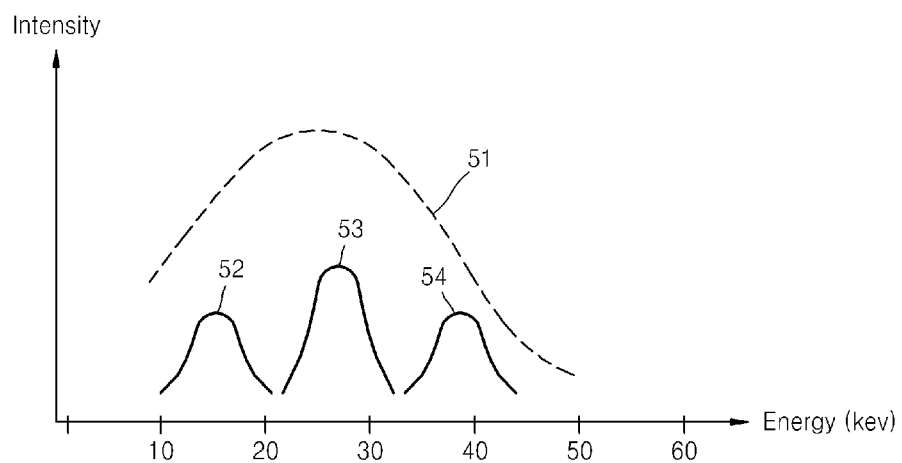
FIG. 5 is a graph illustrating energy spectra of radioactive rays generated by the radiation generator of FIG. 1, according to another example embodiment.

According to another example embodiment, the multi-energy radiation data generating apparatus 10 uses the radiation generator 11 to generate source radioactive rays in different energy bands. FIG. 5 is a graph illustrating energy spectra of radioactive rays generated by the radiation generator 11 of FIG. 1, according to another example embodiment. Referring to FIG. 5, the multi-energy radiation data generating apparatus 10 uses filters inside or outside the radiation generator 11 to generate source radioactive rays 52, 53, and 54 in different energy bands from a source radioactive ray 51 in a single energy band generated by the radiation generator 11. In other words, the multi-energy radiation data generating apparatus 10 uses the radiation generator 11 to generate source radioactive rays in different energy bands in contrast to the example embodiment in which the multi-energy radiation data generating apparatus 10 uses the radiation generator 11 to generate a source radioactive ray in a single energy band. The source radioactive rays in different energy bands may indicate radioactive rays having different peak energy values.

The multi-energy radiation data generating apparatus 10 uses the detector 12 to detect a plurality of radioactive rays in different energy bands that have passed through the subject 40, and generates radiation data corresponding to the plurality of detected radioactive rays. The detector 12 distinguishably detects a plurality of radioactive rays in different energy bands, generates electric signals corresponding to the plurality of detected radioactive rays, and transmits the generated electric signals to the multi-energy radiation data generating apparatus 10. Referring to FIG. 3, the detector 12 uses different filters to detect the radioactive ray in the energy band 31, the radioactive ray in the energy band 32, and the radioactive ray in the energy band 33, generates electrical signals respectively corresponding to the detected radioactive rays, and transmits the generated electrical signals to the multi-energy radiation data generating apparatus 10.

In general, radioactive rays that have passed through the subject 40 indicate only transmit radioactive rays, which have passed through the subject 40, from among primary radioactive rays generated by the radiation generator 11. In other words, the radioactive rays, which have passed through the subject 40, indicate radioactive rays remaining by excluding absorption radioactive rays absorbed by the subject 40, scattering radioactive rays scattered after passing through the subject 40, and radioactive rays emitted as heat energy from the primary radioactive rays.

The multi-energy radiation data generating apparatus 10 generates a plurality of pieces of radiation data respectively corresponding to a plurality of radioactive rays. In this example, each of the plurality of pieces of radiation data indicates fundamental data of a radiation image. For example, when a plurality of devices are arranged in a 2-dimensional (2D) form defined by an x-axis and a y-axis, the multi-energy radiation data generating apparatus 10 uses electric signals generated by the plurality of devices to generate 2D radiation data defined by the x-axis and the y-axis.

In general, a plurality of radioactive rays having different energy bands has different characteristics. For example, a radioactive ray in a high-energy band has a greater transmitting power than a radioactive ray in a low-energy band. However, an energy band, a transmitting power, and an intensity of a radioactive ray do not serve to determine the quality of a radiation image. Even so, since radioactive rays having different energy bands result in radiation images with different characteristics, using radiation images generated from radioactive rays having different energy bands may increase the quality of a radiation image.

The output unit 24 outputs image data of a radiation image generated by the image processor 22 to the image display device 30. The output unit 24 is a kind of interface to connect the image processor 22 and the image display device 30, and the input unit 21 described above is a kind of interface to connect the multi-energy radiation data generating apparatus 10 and the image processor 22. The image display device 30 uses the image data received from the output unit 24 to display a radiation image. An example of the image display device 30 is a device to display a radiation image on a screen or paper, but is not limited thereto.

The storage unit 23 stores various kinds of data generated in image processing performed by the image processor 22. For example, the storage unit 23 stores input multi-energy radiation data, a plurality of pieces of radiation data, and radiation images. Further, according to other example embodiments, the storage unit 23 stores necessary or generated data in computation processes to be described below. The user interface 25 is an interface to receive a command or information from a user, such as, for example, a medical expert and the like. The user interface 25 is generally an input device, such as, for example, a keyboard, a mouse, and the like, and may include a Graphic User Interface (GUI) on the image display device 30.

The image processor 22 uses multi-energy radiation data received from the multi-energy radiation data generating apparatus 10 to generate a radiation image. For example, the image processor 22 uses one or more selected from the group consisting of a plurality of pieces of radiation data included in the multi-energy radiation data to generate a radiation image. In general, each of the plurality of pieces of radiation data includes an intensity difference of a radioactive ray input to the detector 12 according to a radiation transmitting or absorbing power difference between tissues of the subject 40. For example, a component passing through a tissue 401 of the subject 40 and a component passing through another part of the subject 40 in a radioactive ray generated by the radiation generator 11 have different intensities after the radioactive ray passes through the subject 40. These intensity differences are included in radiation data and used by the image processor 22 to generate a radiation image of the subject 40 based on the determined intensity differences. In general, the detector 12 includes an array of a plurality of unit sensors to effectively detect an intensity difference of a radioactive ray input to the detector 12 according to a radiation transmitting or absorbing power difference between tissues of the subject 40. The array of the plurality of unit sensors may be configured variously, such as, for example, a one-dimensional array, a two-dimensional array, a three-dimensional array, and the like.

In general, a radiation transmitting or absorbing power difference between tissues of the subject 40 occurs from a radiation attenuation difference between the tissues of the subject 40. In this example, a degree that each of the tissues attenuates radiation is digitized by an attenuation coefficient, with the attenuation coefficient being represented by an absorption coefficient. In general, an attenuation coefficient decreases as energy of a radioactive ray increases. This may indicate that a radioactive ray in a high-energy band transmits better through the subject 40 compared with a radioactive ray in a low-energy band. In this example, a characteristic that attenuation coefficients of radioactive rays decrease according to a variation of energy bands of the radioactive rays is expressed by the graph shown in FIG. 6.

Figure 6:
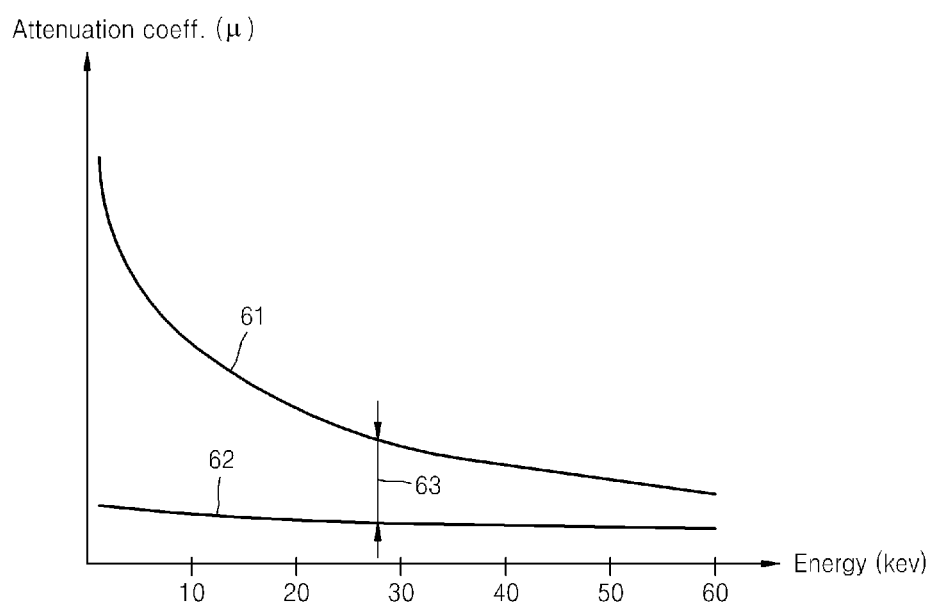
FIG. 6 is a graph illustrating an example of a difference between attenuation coefficients of tissues of a subject.

FIG. 6 is a graph illustrating an example of a difference between attenuation coefficients of tissues of the subject 40. In FIG. 6, reference numeral 61 denotes a general attenuation coefficient variation according to an energy variation of a bone of the tissues of the subject 40, reference numeral 62 denotes a general attenuation coefficient variation according to an energy variation of soft tissue of the tissues of the subject 40, and reference numeral 63 denotes a difference between an attenuation coefficient of the bone and an attenuation coefficient of the soft tissue at a predetermined energy value. In general, as a difference between attenuation coefficients of tissues of the subject 40 increases, a contrast displayed of the difference between the bone and soft tissue in an image increases. However, as described above, the quality of a radiation is not determined solely with respect to an energy band, a transmitting power, and an intensity of a radioactive ray. As is illustrated in FIG. 6, since an attenuation coefficient difference between a bone and soft tissue is sufficient to satisfy a contrast necessary for a radiation image in each energy in a wide energy band (e.g., about 10 keV to about 40 keV), even though a radioactive ray in a predetermined energy band (e.g., about 30 keV to about 40 keV) is used, a contrast between the bone and the soft tissue may be great enough to be clearly displayed in a radiation image.

However, when characteristics of attenuation coefficients of the tissues of the subject 40 are similar to each other, an energy band of a radioactive ray affects the quality of an image. Here, a characteristic of an attenuation coefficient indicates a variation characteristic of the attenuation coefficient according to a variation of energy as described above. For example, when a radiation image of a breast of a patient's soft tissues, such as, for example, a microcalcification tissue, a glandular tissue, an adipose tissue, and a mass or fibrous tissue, is acquired, if a radioactive ray in a higher energy band than a predetermined energy band (e.g., about 20 keV) is used, it is not easy to distinguish the soft tissues from each other in the radiation image.

Figure 7:
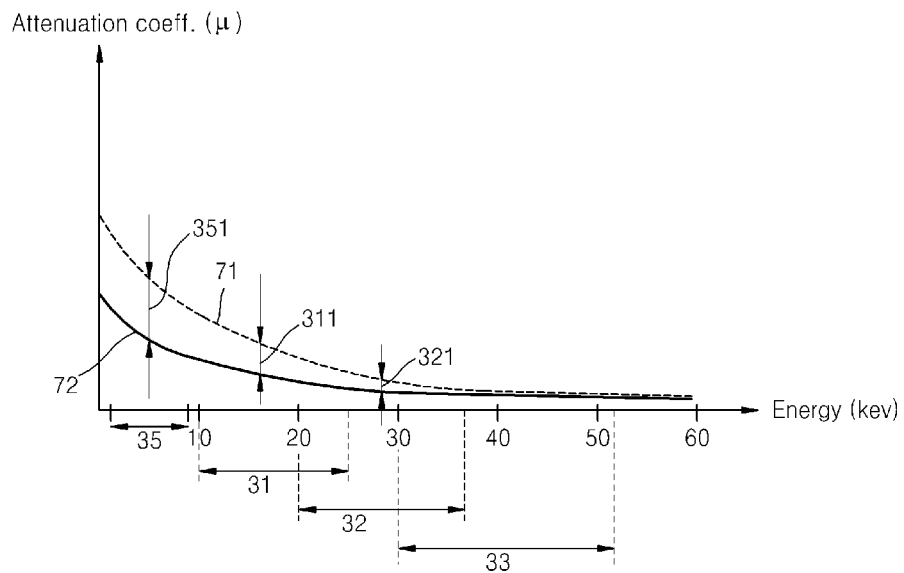
FIG. 7 is a graph illustrating an example of a difference between attenuation coefficients of tissues of the subject when the subject is a human breast.

FIG. 7 is a graph illustrating an example of a difference between attenuation coefficients of human breast tissues of the subject 40. In FIG. 7, reference numeral 71 denotes an attenuation coefficient variation according to an energy variation of a first soft tissue of the subject 40, reference numeral 72 denotes an attenuation coefficient variation according to an energy variation of a second soft tissue of the subject 40, reference numeral 351 denotes a difference between an attenuation coefficient of the first soft tissue and an attenuation coefficient of the second soft tissue at a predetermined energy value in an energy band 35, reference numeral 311 denotes a difference between an attenuation coefficient of the first soft tissue and an attenuation coefficient of the second soft tissue at a predetermined energy value in an energy band 31, and reference numeral 321 denotes a difference between an attenuation coefficient of the first soft tissue and an attenuation coefficient of the second soft tissue at a predetermined energy value in an energy band 32.

As illustrated in FIG. 7, to increase a contrast between the first soft tissue and the second soft tissue of the subject 40, a radioactive ray having the energy band 35, in which a difference between an attenuation coefficient of the first soft tissue and an attenuation coefficient of the second soft tissue is great, is used. However, using a radioactive ray in a low-energy band (e.g., the energy band 35 of FIG. 7) has limitations due to a physical characteristic of the radioactive ray or on an acceptable amount of radiation to which a subject 40 should be exposed. For example, since a radioactive ray in a low-energy band (e.g., the energy band 35 of FIG. 7) has lower transmitting power than a radioactive ray in a high-energy band (e.g., the energy band 32 of FIG. 7), a radiation exposure amount must rise to a value greater than a reference value to generate a radioactive ray having high intensity, but this may be practically impossible due to safety concerns involving the subject 40 and an inability of the detector 12 to adequately detect the physical characteristics of the radioactive ray at the low-energy band.

However, predicting radiation data of a radioactive ray in an energy band that is not generated from radiation data of radioactive rays in different energy bands that are generated may increase contrast of a radiation image. For example, referring to FIG. 7, using radiation data of the respective radioactive rays in the energy band 31 and the energy band 32, which have passed through the subject 40, to predict radiation data of the radioactive ray in the energy band 35 that is not detected by the detector 12 significantly increases contrast between soft tissues of the subject 40.

Referring to FIG. 2, the image processor 22 includes a radiation data generator 221 and a radiation image generator 222. The radiation data generator 221 generates, based on multi-energy radiation data, radiation data of a radioactive ray in an energy band that is different from the different energy bands of the plurality of radioactive rays. The radiation data generator 221, according to an example embodiment, determines an energy band that is different from the different energy bands based on one or more selected from the group consisting of the different energy bands of the plurality of radioactive rays. Referring to FIG. 3, the radiation data generator 221 determines an energy band that is different from the different energy bands based on one or more selected from the group consisting of the energy band 31, the energy band 32, and the energy band 33, which are examples of the different energy bands. Here, an upper limit or a lower limit of the energy band that is different from the different energy bands, which is determined by the radiation data generator 221, may exist in an internal or external area of any one of the different energy bands 31, 32, and 33.

The radiation data generator 221, according to another example embodiment, determines an energy band that is different from the different energy bands based on an entire energy band, the entire energy band being determined by combining the different energy bands of the plurality of radioactive rays. Referring to FIG. 3, the radiation data generator 221 determines an energy band that is different from the different energy bands based on an entire energy band 34, the entire energy band 34 being determined by combining the plurality of energy bands 31, 32, and 33 of the plurality of radioactive rays. Here, an upper limit or a lower limit of the energy band that is different from the different energy bands may exist in an internal or external area of the entire energy band 34. The internal area indicates an internal energy band of the entire energy band 34, and the external area indicates an external energy band of the entire energy band 34.

According to yet another example embodiment, the radiation data generator 221 determines that an upper limit of the energy band that is different from the different energy bands is less than a lower limit of an entire energy band. In other words, the radiation data generator 221 determines a portion of an energy band that is less than the entire energy band to be the energy band that is different from the different energy bands. Referring to FIG. 3, the radiation data generator 221 determines an upper limit of the different energy band 35 to be less than a lower limit of the entire energy band 34. In an example embodiment, the energy band that is different from the different energy bands exists outside of the entire energy band 34.

Figure 8:
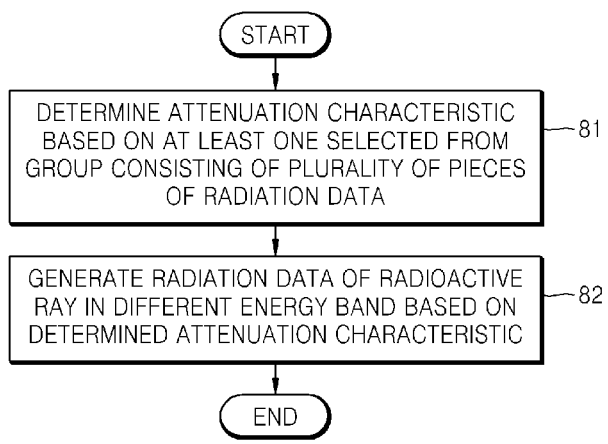
FIG. 8 is a flowchart illustrating a process of generating radiation data by a radiation data generator of FIG. 2, according to an example embodiment.

FIG. 8 is a flowchart illustrating a process of generating radiation data by a radiation data generator 221 of FIG. 2, according to an example embodiment. The radiation data generator 221 determines (81) an attenuation characteristic based on one or more selected from the group consisting of a plurality of pieces of radiation data. The attenuation characteristic indicates a characteristic that an attenuation coefficient of the radioactive ray varies according to a variation of energy. For example, the attenuation characteristic of the radioactive ray indicates a characteristic that an attenuation coefficient of the radioactive ray varies from energy of 0 keV to energy of Emax. In addition, as described above, the attenuation coefficient may be represented by an absorption coefficient. In general, an attenuation coefficient decreases as energy of a radioactive ray increases.

Figure 9:
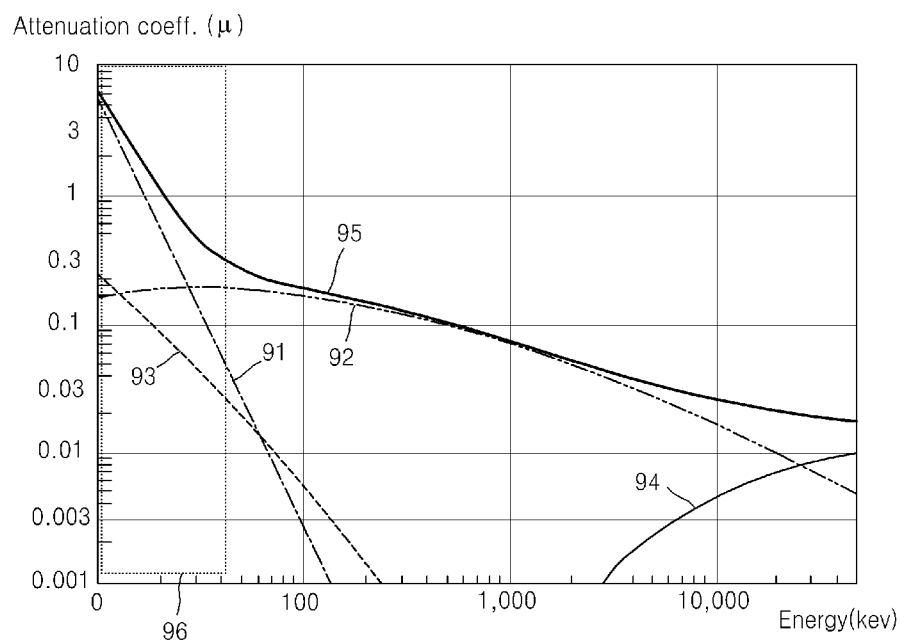
FIG. 9 is a graph illustrating an attenuation characteristic, according to an example embodiment.

FIG. 9 is a graph illustrating an attenuation characteristic, according to an example embodiment. FIG. 9 shows the attenuation characteristic of any one of a plurality of radiation rays having different energy bands. The attenuation characteristic shown in FIG. 9 does not represent all attenuation characteristics of a plurality of radioactive rays having different energy bands. Referring to FIG. 9, a radiation attenuation characteristic 95 is determined from a sum of sub-attenuation characteristics 91 to 94 according to energy bands. In general, the sub-attenuation characteristic 91 is represented by a sub-attenuation characteristic by a photoelectric effect. The photoelectric effect indicates a phenomenon that an electron is emitted from the surface of a material, such as a metal, when a light beam of greater than a predetermined number of vibrations is shone on the material. The sub-attenuation characteristic by the photoelectric effect indicates a characteristic that an attenuation coefficient of a radioactive ray varies according to the photoelectric effect.

In addition, the sub-attenuation characteristic 92 is represented by a sub-attenuation characteristic by Compton scattering. Compton scattering indicates a phenomenon that a photon of a radioactive ray or the like is scattered in a direction different from an original incident direction by being a photon of a number of vibrations that is less than an original number of vibrations. The sub-attenuation characteristic by the Compton scattering indicates a characteristic that an attenuation coefficient of a radioactive ray varies according to the Compton scattering.

Moreover, the sub-attenuation characteristic 93 is represented by a sub-attenuation characteristic by Rayleigh scattering. Rayleigh scattering indicates scattering of light of a long wavelength occurring when a bound electron is in an excited state, by virtually absorbing light of a greater wavelength than that of an atom, and, then, returns to its original state. The sub-attenuation characteristic by the Rayleigh scattering indicates a characteristic that an attenuation coefficient of a radioactive ray varies according to the Rayleigh scattering.

Further, the sub-attenuation characteristic 94 is represented by a sub-attenuation characteristic by electron-pair production. Electron-pair production indicates a phenomenon that a photon of energy greater than about 1.02 MeV is changed to an electron pair of a negatron and a positron by being affected by a strong electric field when the photon passes around an atomic core of a material. The sub-attenuation characteristic by the electron-pair production indicates a characteristic that an attenuation coefficient of a radioactive ray varies according to the electron-pair production.

As described above with reference to FIG. 9, the radiation attenuation characteristic 95 is determined from a sum of the sub-attenuation characteristics 91 to 94 according to energy bands. However, in general, when a variation of a radiation attenuation characteristic is determined, because the sub-attenuation characteristic by the photoelectric effect and the sub-attenuation characteristic by the Compton scattering affect the variation of the radiation attenuation characteristic 95 to a much greater extent than other sub-attenuation characteristics, the variation of a radiation attenuation characteristic may be defined by a sum of the sub-attenuation characteristic by the photoelectric effect and the sub-attenuation characteristic by the Compton scattering. Referring to FIG. 9, the radiation attenuation characteristic 95 determined from a sum of the sub-attenuation characteristics 91 to 94 approximates the radiation attenuation characteristic 95 determined from a sum of the sub-attenuation characteristics 91 and 92. The radiation attenuation characteristic 95 of FIG. 9 is expressed by Equation 1.

$$\mu_{Total} = \mu_{CS} + \mu_{PE} + \mu_{RS} + \mu_{PP} \quad \text{[Equation 1]}$$
$$\approx \mu_{CS} + \mu_{PE}$$

In Equation 1, $\mu_{Total}$ denotes the radiation attenuation characteristic 95 of FIG. 9, $\mu_{cs}$ denotes the sub-attenuation characteristic 92 by the Compton scattering of FIG. 9, $\mu_{PE}$ denotes the sub-attenuation characteristic 91 by the photoelectric effect of FIG. 9, $\mu_{RS}$ denotes the sub-attenuation characteristic 93 by the Rayleigh scattering, and $\mu_{PP}$ denotes the sub-attenuation characteristic 94 by the electron-pair production.

In general, as shown in FIG. 9, the attenuation characteristic by the photoelectric effect maintains linearity in a predetermined energy band. The fact that the attenuation characteristic by the photoelectric effect maintains linearity indicates that the attenuation characteristic by the photoelectric effect maintains linearity according to a variation of energy when the attenuation characteristic by the photoelectric effect is analyzed in a log domain and in a predetermined energy band 96.

In addition, the attenuation characteristic by the Compton scattering is constantly maintained in a predetermined range of attenuation coefficients according to a variation of energy in the predetermined energy band. Referring to FIG. 9, the fact that the attenuation characteristic by the Compton scattering is maintained constantly may indicate that the sub-attenuation characteristic 92 by the Compton scattering is maintained similarly based on a predetermined attenuation coefficient according to a variation of energy in the predetermined energy band 96.

The radiation data generator 221 predicts an attenuation characteristic based on radiation data of one or more selected from the group consisting of the plurality of radioactive rays in different energy bands. Each of the plurality of radioactive rays in different energy bands is distinguishably detected from the same source radioactive ray. Thus, attenuation characteristics of the plurality of radioactive rays are substantially the same. In other words, the radiation data generator 221 determines a variation characteristic of attenuation coefficients based on radiation data of one or more selected from the group consisting of the plurality of radioactive rays in different energy bands.

The radiation data generator 221 generates (82) the radiation data of the radioactive ray in the energy band that is different from the different energy bands based on the determined attenuation characteristic. For example, the radiation data generator 221 determines an attenuation coefficient in the energy band that is different from the different energy bands from the determined attenuation characteristic (e.g., a variation characteristic of attenuation coefficients of the plurality of radioactive rays) and generates radiation data in the energy band that is different from the different energy bands based on the determined attenuation coefficient. At this time, the radiation data generator 221 generates radiation data in the energy band that is different from the different energy bands based on the linearity of the determined attenuation characteristic. The linearity may indicate linearity in the log domain.

Figure 10:
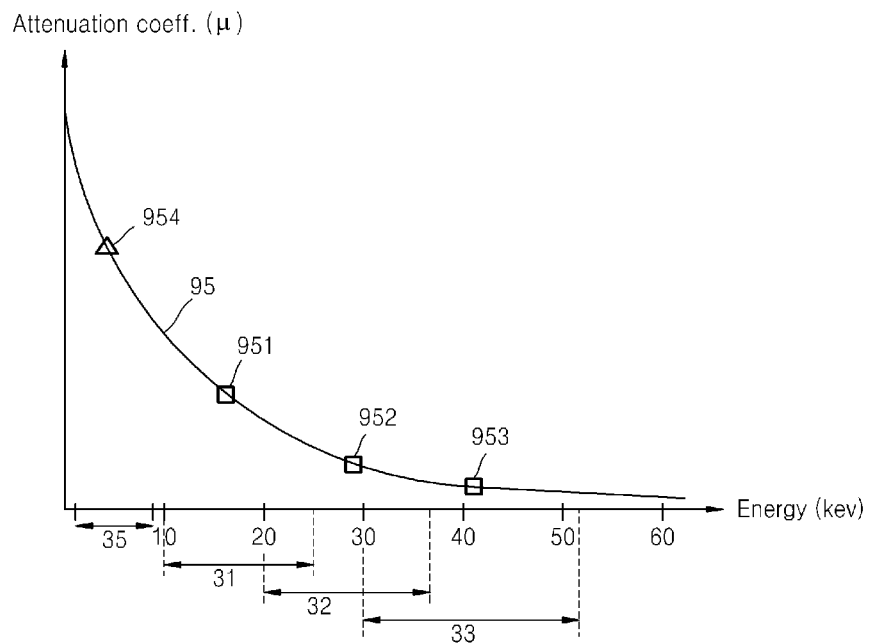
FIG. 10 is a graph illustrating an example of a variation characteristic of the attenuation characteristic of FIG. 9 in an energy band of FIG. 9.

FIG. 10 is a graph illustrating an example of a variation characteristic of the attenuation characteristic 95 of FIG. 9 in an energy band 96 of FIG. 9. When a unit of energy in the graph of FIG. 10 varies in log units, the attenuation characteristic 95 of FIG. 10 may be changed to a linear graph in a form of a direct line. Referring to FIG. 10, the radiation data generator 221 determines an attenuation characteristic by using radiation data of one or more selected from the group consisting of the radioactive ray in the energy band 31, the radioactive ray in the energy band 32, and the radioactive ray in the energy band 33, determines an attenuation coefficient in the energy band 35 that is different from the different energy bands based on the determined attenuation characteristic, and generates radiation data in the energy band 35 that is different from the different energy bands based on the determined attenuation coefficient. For example, the radiation data generator 221 determines an attenuation coefficient 951 of the radioactive ray in the energy band 31 and an attenuation coefficient 952 of the radioactive ray in the energy band 32 by using the radiation data of the radioactive ray in the energy band 31 and the radiation data of the radioactive ray in the energy band 32, respectively, determines an attenuation characteristic based on the determined attenuation coefficients 951 and 952, determines an attenuation coefficient 954 in the energy band 35 that is different from the different energy bands based on the determined attenuation characteristic, and generates radiation data in the energy band 35 that is different from the different energy bands based on the determined attenuation coefficient 954. In this case, to determine the attenuation characteristic based on the determined attenuation coefficients 951 and 952, the linearity of an attenuation characteristic described above may be used. The determination of an attenuation coefficient by using radiation data indicates determining the attenuation coefficient by using radiation intensity included in the radiation data. The generation of radiation data from the attenuation coefficient indicates generating radiation intensity included in the radiation data from the attenuation coefficient.

In general, a relational expression, such as Equation 2, is established between radiation intensity and a radiation attenuation coefficient.

$$I(\mu, t, E) = -\ln(\int_E I_0(E) \cdot \exp(-\Sigma \mu_k(E) \cdot t_k) dE) \quad \text{[Equation 2]}$$

In Equation 2, k denotes the kind of a material through which a radioactive ray transmits (e.g., the kind of soft tissue of the human body), $t_k$ denotes the thickness of the material through which the radioactive ray transmits, $\mu_k$ denotes a radiation attenuation characteristic according to the kind of the material through which the radioactive ray transmits, and/denotes radiation intensity detected by the detector 12.

According to an example embodiment, the radiation data generator 221 determines the radiation attenuation coefficient 951 in the energy band 31 and the radiation attenuation coefficient 952 in the energy band 32 by using the radiation intensity in the energy band 31 and the radiation intensity in the energy band 32 based on Equation 2, respectively, determines an attenuation characteristic based on the determined attenuation coefficients 951 and 952, determines the attenuation coefficient 954 in the different energy band 35 based on the determined attenuation characteristic, and generates radiation intensity in the different energy band 35 based on the determined attenuation coefficient 954. In this case, to determine the attenuation characteristic based on the determined attenuation coefficients 951 and 952, the linearity of an attenuation characteristic described above may be used.

In an example, while determining the attenuation characteristic and generating the radiation data of the radioactive ray in the energy band that is different from the different energy bands, the radiation data generator 221 uses reference information stored in the storage unit 23. The reference information may indicate previous index information or generalized previous information. For example, the storage unit 23 previously stores general relationships between attenuation coefficients, attenuation characteristics, and radiation intensities based on a plurality of pieces of raw data. The radiation data generator 221 determines the attenuation characteristic and generates the radiation data of the radioactive ray in the energy band that is different from the different energy bands, or corrects or verifies results of the determining of the attenuation characteristic and the generating of the radiation data of the radioactive ray in the energy band that is different from the different energy bands, based on data stored in the storage unit 23. For example, the radiation data generator 221 reads an attenuation characteristic from the storage unit 23 by inputting radiation data of one or more selected from the group consisting of radioactive rays in different energy bands to the storage unit 23 and reads radiation data of a radioactive ray in the energy band that is different from the different energy bands from the storage unit 23 by inputting the read attenuation characteristic and the energy band that is different from the different energy bands to the storage unit 23. As another example, the radiation data generator 221 reads radiation data of a radioactive ray in the energy band that is different from the different energy bands from the storage unit 23 by inputting radiation data of one or more selected from the group consisting of radioactive rays in different energy bands to the storage unit 23.

Figure 11:
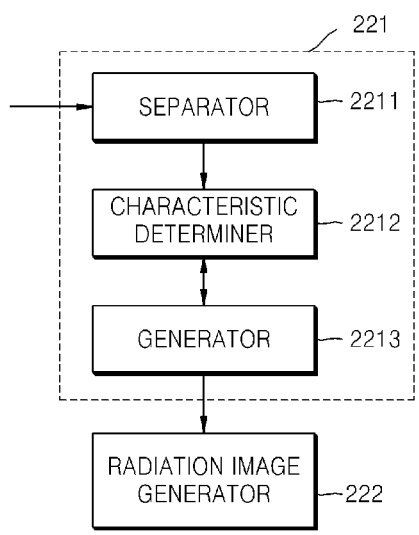
FIG. 11 is a block diagram illustrating the radiation data generator of FIG. 2, according to an example embodiment.

FIG. 11 is a block diagram illustrating the radiation data generator 221 of FIG. 2, according to an example embodiment. Referring to FIG. 11, the radiation data generator 221 includes a separator 2211, a characteristic determiner 2212, and a generator 2213. The separator 2211 extracts the intensity of a pixel from each of a plurality of pieces of radiation data respectively corresponding to a plurality of radioactive rays in different energy bands. The pixel indicates any one of a plurality of pixels included in each of the plurality of pieces of radiation data. Although only one pixel is described hereinafter for convenience of description, the same operation applies to all pixels.

In general, intensity includes one or more selected from the group consisting of intensity by the photoelectric effect and intensity by the Compton scattering. The intensity by the photoelectric effect is a concept corresponding to the attenuation coefficient by the photoelectric effect described above, and the intensity by the Compton scattering is a concept corresponding to the attenuation coefficient by the Compton scattering described above.

As described above, a relationship between a radiation attenuation coefficient and radiation intensity is expressed by Equation 2. In addition, as described above, a relationship between an attenuation coefficient by the photoelectric effect and an attenuation coefficient by the Compton scattering and a radiation attenuation coefficient is expressed by Equation 1. Thus, a relationship between an attenuation coefficient by the photoelectric effect and an attenuation coefficient by the Compton scattering and radiation intensity is expressed by Equation 3 based on Equations 1 and 2. In addition, Equation 3 further expresses a relationship between intensity by the photoelectric effect and intensity by the Compton scattering and radiation intensity.

$$I(\mu_{PE} + \mu_{CS}, t, E) \cong \alpha \cdot I_{PE} + \beta \cdot I_{CS} \quad \text{[Equation 3]}$$

In Equation 3, t denotes the thickness of a material, I denotes radiation intensity, $I_{PE}$ denotes intensity by the photoelectric effect, $I_{CS}$ denotes intensity by the Compton scattering, $\alpha$ denotes a constant, $\beta$ denotes another constant different from $\alpha$, $\mu_{PE}$ denotes an attenuation coefficient by the photoelectric effect, and $\mu_{CS}$ denotes an attenuation coefficient by the Compton scattering. Referring to Equation 3, for example, radiation intensity is determined from a sum of intensity by the photoelectric effect to which a predetermined constant is applied and intensity by the Compton scattering to which another predetermined constant is applied.

Figure 12:
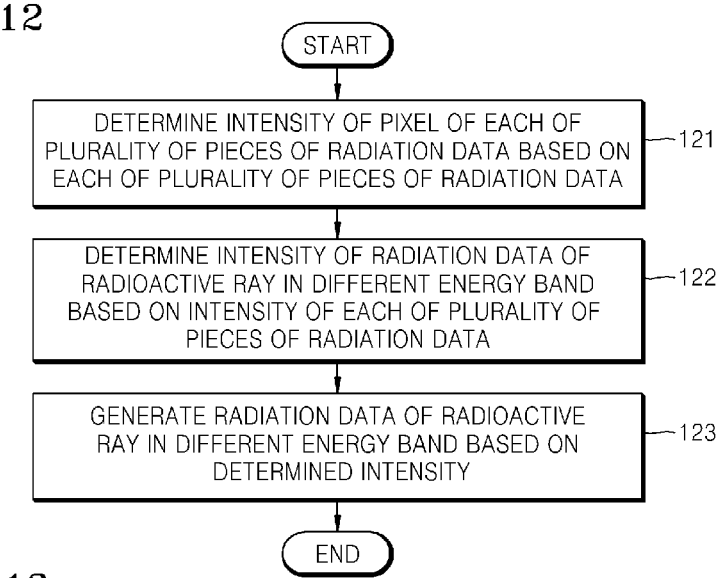
FIG. 12 is a flowchart illustrating a process of generating radiation data of a radioactive ray in an energy band that is different from different energy bands by a characteristic determiner and a generator of FIG. 11, according to an example embodiment.

FIG. 12 is a flowchart illustrating a process of generating radiation data of a radioactive ray in the energy band that is different from the different energy bands by a characteristic determiner 2212 and a generator 2213 of FIG. 11, according to an example embodiment. Referring to FIG. 12, the characteristic determiner 2212 determines (121) the intensity of a pixel in each of a plurality of pieces of radiation data based on the plurality of pieces of radiation data respectively corresponding to a plurality of radioactive rays in different energy bands. As described above, each of the plurality of pieces of radiation data includes intensities of a plurality of pixels in each of the plurality of pieces of radiation data. Thus, it is possible that the characteristic determiner 2212 extracts the intensity of a pixel from each of the plurality of pieces of radiation data in the different energy bands. In addition, as described above, the intensity of a pixel is detected by the detector 12.

Referring to FIG. 3, from among the plurality of pieces of radiation data, the characteristic determiner 2212 extracts first intensity from first radiation data in the energy band 31, second intensity from second radiation data in the energy band 32, and third intensity from third radiation data in the energy band 33.

The characteristic determiner 2212 determines (122) intensity of radiation data of a radioactive ray in the energy band that is different from the different energy bands based on the intensity of each of the plurality of pieces of radiation data. As described above, the intensity of a pixel is defined by intensity by the photoelectric effect and intensity by the Compton scattering. In addition, the intensity by the photoelectric effect has substantially the same variation characteristic as that of an attenuation characteristic by the photoelectric effect, and the intensity by the Compton scattering has substantially the same variation characteristic as that of an attenuation characteristic by the Compton scattering. Thus, the intensity by the photoelectric effect maintains linearity. The fact that the intensity by the photoelectric effect maintains linearity may indicate that the intensity by the photoelectric effect maintains linearity according to a variation of energy when the intensity by the photoelectric effect is analyzed in the log domain. In addition, the intensity by the Compton scattering is constantly maintained in a predetermined range of attenuation coefficients according to a variation of energy. The fact that the intensity by the Compton scattering is constantly maintained may indicate that the intensity by the Compton scattering is maintained similarly based on a predetermined intensity according to a variation of energy in a predetermined energy band.

The characteristic determiner 2212 determines intensity by the photoelectric effect and intensity by the Compton scattering of each of the plurality of pieces of radiation data based on intensity of each of the plurality of pieces of radiation data and determines intensity of radiation data of a radioactive ray in the energy band that is different from the different energy bands based on the determined intensity by the photoelectric effect and the determined intensity by the Compton scattering. That is, as described above, the characteristic determiner 2212 determines intensity by the photoelectric effect and intensity by the Compton scattering of each of the plurality of pieces of radiation data by using the fact that linearity is maintained between the intensities by the photoelectric effect of the plurality of pieces of radiation data and the fact that the intensities by the Compton scattering of the plurality of pieces of radiation data are maintained to be substantially the same to each other. As a result, the characteristic determiner 2212 determines intensity of radiation data of a radioactive ray in the energy band that is different from the different energy bands based on the determined intensity by the photoelectric effect and the determined intensity by the Compton scattering.

Figure 13:
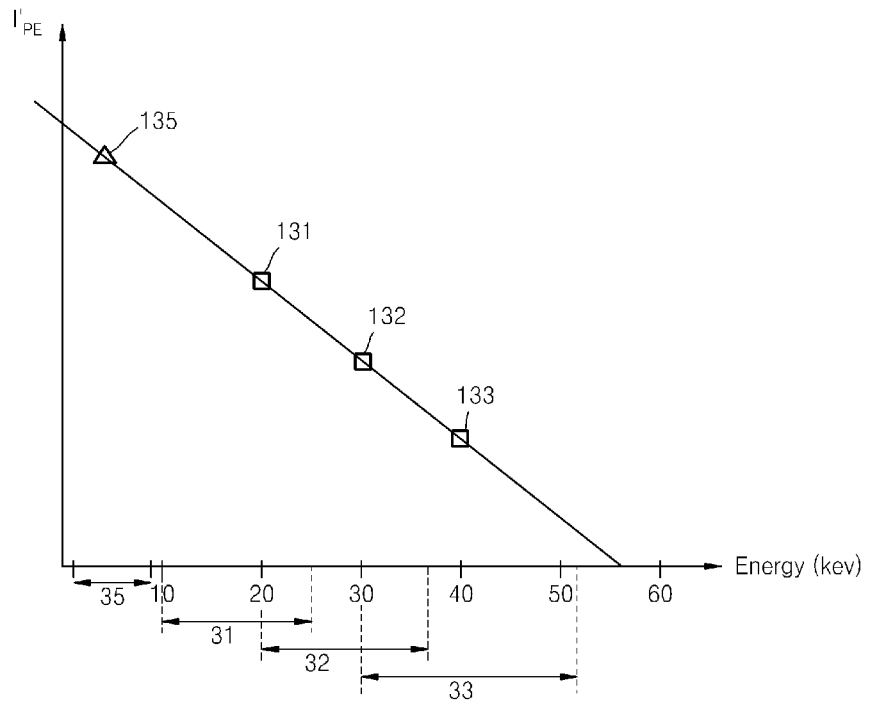
FIG. 13 is a graph illustrating an example of a state in which linearity is maintained between intensities by a photoelectric effect of a plurality of pieces of radiation data in different energy bands.

FIG. 13 is a graph illustrating an example of a state in which linearity is maintained between intensities by a photoelectric effect of a plurality of pieces of radiation data in different energy bands. Referring to FIG. 13, according to an example embodiment, the characteristic determiner 2212 determines intensities by the Compton scattering of a plurality of radioactive rays as a predetermined constant based on the fact that intensities by the Compton scattering of a plurality of pieces of radiation data (e.g., the radiation data in the energy band 31, the radiation data in the energy band 32, and the radiation data in the energy band 33) are maintained to be substantially the same to each other in a predetermined energy band range. In addition, the characteristic determiner 2212 defines, as is provided in Equation 4, a relationship between intensity by the Compton scattering of each of the plurality of pieces of radiation data (e.g., the radiation data in the energy band 31, the radiation data in the energy band 32, and the radiation data in the energy band 33), intensity of each of the plurality of pieces of radiation data, and variable intensity by the photoelectric effect of each of the plurality of pieces of radiation data.

$$I'_{PE} = \log(I - w_i I_{CS})$$ [Equation 4]

In Equation 4, $I_{CS}$ denotes intensity by the Compton scattering of any one of the plurality of pieces of radiation data (e.g., the radiation data in the energy band 31, the radiation data in the energy band 32, and the radiation data in the energy band 33), I denotes intensity of any one of the plurality of pieces of radiation data, $w_i$ denotes a predetermined coefficient, and $I'_{PE}$ denotes variable intensity by the photoelectric effect of any one of the plurality of pieces of radiation data.

Referring to FIG. 13, the characteristic determiner 2212 determines intensity by the Compton scattering of the first radiation data in the energy band 31, intensity by the Compton scattering of the second radiation data in the energy band 32, and intensity by the Compton scattering of the third radiation data in the energy band 33 as a predetermined constant. As described above, the predetermined constant is determined by the characteristic determiner 2212 according to the fact that intensities by the Compton scattering have substantially the same values in a predetermined energy band range.

In addition, according to another example embodiment, the characteristic determiner 2212 uses reference information stored in the storage unit 23 to determine a constant. In this example, the characteristic determiner 2212 inputs one or more selected from the group consisting of the first radiation data in the energy band 31, the second radiation data in the energy band 32, and the third radiation data in the energy band 33 to the storage unit 23, and reads a constant from the storage unit 23.

Referring to FIG. 13, according to an example embodiment, the characteristic determiner 2212 determines $w_i$ satisfying linearity between variable intensity by the photoelectric effect of the first radiation data in the energy band 31, variable intensity by the photoelectric effect of the second radiation data in the energy band 32, and variable intensity by the photoelectric effect of the third radiation data in the energy band 33 based on $I_{CS}$ determined from Equation 4, which is determined by the characteristic determiner 2212 to be intensity by the Compton scattering of the first radiation data in the energy band 31, intensity by the Compton scattering of the second radiation data in the energy band 32, and intensity by the Compton scattering of the third radiation data in the energy band 33. The intensity by the Compton scattering of the first radiation data in the energy band 31, intensity by the Compton scattering of the second radiation data in the energy band 32, and intensity by the Compton scattering of the third radiation data in the energy band 33 are detected by the detector 12.

In addition, the characteristic determiner 2212 determines intensity 131 by the photoelectric effect of the first radiation data in the energy band 31, intensity 132 by the photoelectric effect of the second radiation data in the energy band 32, and intensity 133 by the photoelectric effect of the third radiation data in the energy band 33 based on $I_{CS}$ determined from Equation 4, the intensity by the Compton scattering of the first radiation data in the energy band 31, the intensity by the Compton scattering of the second radiation data in the energy band 32, and the intensity by the Compton scattering of the third radiation data in the energy band 33, and the determined $w_i$.

Further, according to another example embodiment, the characteristic determiner 2212 uses reference information stored in the storage unit 23 to determine $w_i$, the intensity 131 by the photoelectric effect of the first radiation data, the intensity 132 by the photoelectric effect of the second radiation data, and the intensity 133 by the photoelectric effect of the third radiation data.

Referring to FIG. 13, according to an example embodiment, the characteristic determiner 2212 determines intensity 135 by the photoelectric effect of the radiation data in the energy band 35 that is different from the different energy bands and intensity by the Compton scattering of the radiation data in the energy band 35 that is different from the different energy bands based on one or more selected from the group consisting of the intensity by the Compton scattering of the first radiation data in the energy band 31, the intensity by the Compton scattering of the second radiation data in the energy band 32, the intensity by the Compton scattering of the third radiation data in the energy band 33, $w_i$, the intensity 131 by the photoelectric effect of the first radiation data, the intensity 132 by the photoelectric effect of the second radiation data, and the intensity 133 by the photoelectric effect of the third radiation data. The characteristic determiner 2212 determines radiation intensity in the energy band 35 that is different from the different energy bands based on the intensity 135 by the photoelectric effect of the radiation data in the energy band 35 that is different from the different energy bands and the intensity by the Compton scattering of the radiation data in the energy band 35 that is different from the different energy bands.

In this case, the energy band 35 that is different from the different energy bands may be pre-defined or input by using the user interface 25, and the characteristic determiner 2212 may perform the above-described computations based on one or more selected from the group consisting of energy values belonging to the energy band 35 that is different from the different energy bands. In addition, according to another example embodiment, the characteristic determiner 2212 uses reference information stored in the storage unit 23 to determine the intensity 135 by the photoelectric effect of the radiation data in the energy band 35 that is different from the different energy bands and the intensity by the Compton scattering of the radiation data in the energy band 35 that is different from the different energy bands.

The generator 2213 generates (123) the radiation data of the radioactive ray in the energy band that is different from the different energy bands based on the determined intensity. As described above, the determined intensity is intensity of any one of a plurality of pixels, and the generator 2213 uses intensities of the plurality of pixels to generate the radiation data in the energy band that is different from the different energy bands. Referring to FIG. 13, the generator 2213 generates radiation data corresponding to the radioactive ray in the energy band 35 that is different from the different energy bands based on the determined intensity 135.

The radiation image generator 222 generates a radiation image of the subject 40 based on the generated radiation data. As a result, in accordance with the teachings above, the radiation image generator 222 generates a radiation image corresponding to a radioactive ray in an energy band that is not detected by the detector 12. Referring to FIG. 3, even though the radiation data of the radioactive ray in the energy band 35 that is different from the different energy bands is not input, the radiation image generator 222 generates a radiation image corresponding to the radioactive ray in the energy band 35 that is different from the different energy bands, which, based on the plurality of pieces of radiation data in the different energy bands that are different from the energy band 35, possesses a characteristic different from that of a radiation image corresponding to the radioactive ray in the energy band 31, a radiation image corresponding to the radioactive ray in the energy band 32, a radiation image corresponding to the radioactive ray in the energy band 33, or a radiation image corresponding to a radioactive ray in the entire energy band 34.

According to another example embodiment, the radiation image generator 222 generates a radiation image of the subject 40 based on the generated radiation data and one or more selected from the group consisting of the plurality of pieces of radiation data. For example, the radiation image generator 222 uses one or more selected from the group consisting of the plurality of pieces of radiation data to generate a first radiation image of the subject 40, uses the generated radiation data to generate a second radiation image of the subject 40, and generates the radiation image of the subject 40 based on the first radiation image and the second radiation image. At this time, the radiation image generator 222 determines pixel information of each of pixels of the radiation image based on pixel information of each of first pixels of the first radiation image and pixel information of each of second pixels of the second radiation image. For example, to determine pixel information of any one of the pixels, the radiation image generator 222 subtracts pixel information of any one of the second pixels from pixel information of any one of the first pixels or calculates an average of pixel information of any one of the first pixels and pixel information of any one of the second pixels.

Figure 14:
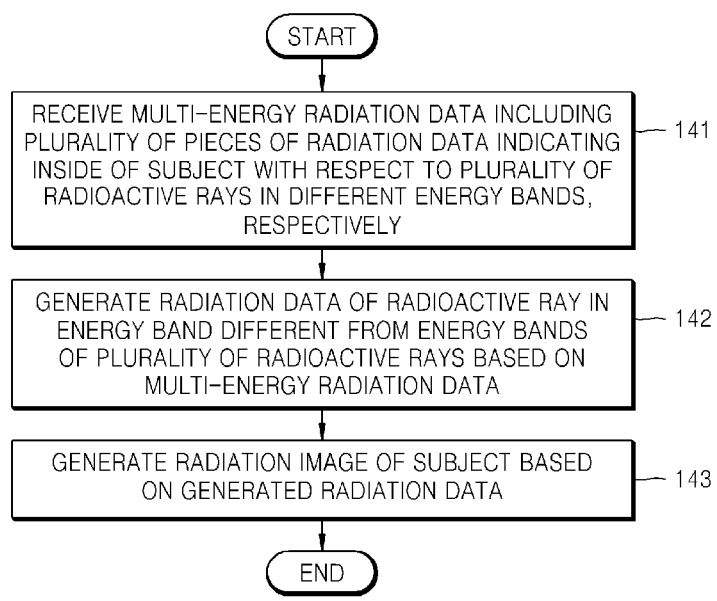
FIG. 14 is a flowchart illustrating a method of generating a radiation image, according to an example embodiment.

FIG. 14 is a flowchart illustrating a method of generating a radiation image, according to an example embodiment. Referring to FIG. 14, in the example embodiment, the method is performed by the radiation image generating apparatus 20 of FIG. 2. Thus, although omitted below, in an example embodiment, the above description of the radiation image generating apparatus 20 of FIG. 2 also applies to the method of FIG. 14.

The input unit 21 receives (141) multi-energy radiation data including a plurality of pieces of radiation data indicating an inner portion of a subject with respect to a plurality of radioactive rays in different energy bands, respectively. The radiation data generator 221 generates (142) radiation data in an energy band different from the energy bands of the plurality of radioactive rays based on the received multi-energy radiation data. The radiation image generator 222 generates (143) a radiation image of the subject based on the generated radiation data.

According to the teachings above, provided are a radiation image generating method and apparatus that, by generating radiation data of radioactive rays in an energy band different from energy bands of a plurality of radioactive rays from a plurality of pieces of radiation data corresponding to the plurality of radioactive rays in the respective energy bands, may be capable of securing radiation data in an energy band difficult to use for a patient due to a physical characteristic of the energy band. In addition, provided are a radiation image generating method and apparatus that, by generating radiation data in a low-energy band from a plurality of pieces of radiation data in different energy bands and generating a radiation image based on the generated radiation data in the low-energy band, may be capable of using a contrast-enhanced radiation image for diagnosis. In addition, provided are a radiation image generating method and apparatus that, by determining an attenuation characteristic of radiation data in different energy bands and generating the radiation data in the low-energy band based on the determined attenuation characteristic, may be capable of correctly and efficiently generating radiation data in a low-energy band. As a result, the radiation image corresponding to the radioactive ray in the energy band that is different from the different energy bands may provide a higher contrast or better quality that those of other above-described radiation images.

The units described herein may be implemented using hardware components and software components, such as, for example, microphones, amplifiers, band-pass filters, audio to digital converters, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium, or device or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. In addition, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of generating a radiation image, the method comprising:
   receiving multi-energy radiation data comprising a plurality of pieces of radiation data indicating an inner portion of a subject with respect to a plurality of radioactive rays in different energy bands, respectively;
   generating, based on the received multi-energy radiation data, radiation data of a radioactive ray in an energy band that is distinct from the different energy bands; and
   generating a radiation image of the subject based on the generated radiation data,
   wherein the energy band that is distinct from the different energy bands is determined based on an entire energy band, the entire energy band being determined by combining the different energy bands of the plurality of radioactive rays, and
   wherein the energy band that is distinct from the different energy bands exists outside of the entire energy band, and
   wherein the energy band that is distinct from the different energy bands is determined based on one or more of the different energy bands of the plurality of radioactive rays.

2. The method of claim 1, wherein an upper limit of the energy band that is distinct from the different energy bands is less than a lower limit of the entire energy band.

3. The method of claim 1, wherein the generating of the radiation data comprises determining an attenuation characteristic and generating the radiation data of the radioactive ray in the energy band that is distinct from the different energy bands based on the determined attenuation characteristic, the determining of the attenuation characteristic being based on one or more selected from the group consisting of the plurality of pieces of radiation data.

4. The method of claim 3, wherein the generated radiation data of the radioactive ray in the energy band that is distinct from the different energy bands is based on linearity of the determined attenuation characteristic.

5. The method of claim 4, wherein the determined attenuation characteristic comprises at least one of an attenuation characteristic by a photoelectric effect and an attenuation characteristic by Compton scattering.

6. The method of claim 1, wherein the generating of the radiation data comprises
    determining an intensity of a pixel for each of the plurality of pieces of radiation data, the intensity of the pixel being based on each of the plurality of pieces of radiation data,
    determining an intensity of the radiation data of the radioactive ray in the energy band that is distinct from the different energy bands, based on the intensity of each of the plurality of pieces of radiation data, using intensities of pixels associated with the plurality of pieces of radiation data, and
    generating the radiation data of the radioactive ray in the energy band that is distinct from the different energy bands based on the determined intensity of the radiation data.

7. The method of claim 6, wherein the determining of the intensity of the pixel comprises determining first intensity of first radiation data of the plurality of pieces of radiation data and determining second intensity of second radiation data of the plurality of pieces of radiation data, and
    wherein the determining of the intensity of the radiation data comprises determining intensity of the radioactive ray in the energy band that is distinct from the different energy bands based on linearity between the determined first intensity and the determined second intensity.

8. The method of claim 7, wherein the intensity comprises at least one of intensity by a photoelectric effect and intensity by Compton scattering.

9. The method of claim 1, wherein the plurality of radioactive rays in the different energy bands is detected on an energy band basis from a radioactive ray that has passed through the subject.

10. The method of claim 1, wherein the plurality of radioactive rays in the different energy bands have different peak energy values.

11. The method of claim 1, wherein the generating of the radiation image comprises generating a radiation image of the subject based on at least one of pieces of radiation data and the generated radiation data.

12. The method of claim 11, wherein the generating of the radiation image further comprises generating a first radiation image of the subject, generating a second radiation image of the subject, and generating the radiation image of the subject based on the first radiation image and the second radiation image, the generating of the first radiation image being performed by using one or more pieces of radiation data, the generating of the second radiation image being performed by using the generated radiation data.

13. A non-transitory computer-readable recording medium storing a computer-readable program for executing the method of claim 1.

14. An apparatus to generate a radiation image, the apparatus comprising: an input unit processor configured to receive multi-energy radiation data comprising a plurality of pieces of radiation data indicating an inner portion of a subject with respect to a plurality of radioactive rays in different energy bands, respectively; an image processor configured to generate radiation data of a radioactive ray in an energy band that is distinct from the different energy bands and a radiation image of the subject based on the generated radiation data, the generated radiation data being based on the received multi-energy radiation data, wherein the energy band that is distinct from the different energy bands is determined based on an entire energy band, the entire energy band being determined by combining the different energy bands of the plurality of radioactive rays and wherein the entire energy band that is distinct from the different energy bands exists outside of the entire energy band, and wherein the energy band that is distinct from the different energy bands is determined based on one or more of the different energy bands of the plurality of radioactive rays; and an output processor configured to output the generated radiation image.

15. The apparatus of claim 14, wherein the image processor comprises a radiation data generator and a radiation image generator, the radiation data generator being configured to generate, based on the received multi-energy radiation data, the radiation data of the radioactive ray in the energy band that is distinct from the different energy bands, and the radiation image generator being configured to generate the radiation image of the subject based on the generated radiation data.

16. The apparatus of claim 15, wherein the radiation data generator comprises a separator, a characteristic determiner, and a generator, the separator being configured to extract each of the plurality of pieces of radiation data from the received multi-energy radiation data, the characteristic determiner being configured to determine an attenuation characteristic based on one or more pieces of extracted radiation data, and the generator being configured to generate radiation data of the plurality of radioactive rays in the different energy bands based on the determined attenuation characteristic.

17. The apparatus of claim 15, wherein the radiation image of the subject is generated based on at least one of the plurality of pieces of radiation data and the generated radiation data.

* * * * *